United States Patent [19]

Duffy et al.

[11] Patent Number: 4,898,826

[45] Date of Patent: Feb. 6, 1990

[54] METHOD TO SOLUBILIZE TISSUE PLASMINOGEN ACTIVATOR

[75] Inventors: Stephen A. Duffy, Florissant; Christopher P. Prior, Ballwin, both of Mo.; Randal W. Scott, Sunnyvale, Calif.

[73] Assignee: Invitron Corporation, St. Louis, Mo.

[21] Appl. No.: 130,901

[22] Filed: Dec. 10, 1987

[51] Int. Cl.[4] .................. C12N 9/64; C12N 9/48; C12N 9/50; A61K 37/547
[52] U.S. Cl. ..................... 435/226; 435/212; 435/219; 424/94.64
[58] Field of Search ............... 435/212, 219, 226; 424/94.64

[56] References Cited

U.S. PATENT DOCUMENTS 4,568,544 2/1986 Hasegawa et al. ............ 424/94
4,777,043 10/1988 Bennett et al. ............ 424/94.64

FOREIGN PATENT DOCUMENTS 0217379 4/1987 European Pat. Off. .
0245100 11/1987 European Pat. Off. .

OTHER PUBLICATIONS

Rijken et al., (1979) Biochi. Biophys. Acta 580:140-153.
Pennica et al., (1983) Nature 301:214-221.

Primary Examiner—Thomas G. Wiseman
Assistant Examiner—Charles L. Patterson, Jr.
Attorney, Agent, or Firm—Irell & Manella

[57] ABSTRACT

Practical amounts of tissue plasminogen activator (tPA) whether secreted by cells naturally producing it or prepared by recombinant means can be solubilized by providing, in aqueous medium at pH 5-8 a solubilizing amount of a basic amino acid optionally and preferably, in the presence of a citric acid moiety. The ability to solubilize tPA at concentrations of up to 50 mg is significant as an aid in permitting smaller volumes for purification and permitting single injections of the drug as opposed to intravenous administration.

8 Claims, No Drawings

METHOD TO SOLUBILIZE TISSUE PLASMINOGEN ACTIVATOR

TECHNICAL FIELD

The invention relates to the purification and formulation of tissue plasminogen activator (tPA). In particular, it concerns the use of arginine/citrate buffer to effect high solubility properties on the normally insoluble material.

BACKGROUND ART

Tissue plasminogen activator (tPA) is an extremely promising drug which can be used to dissolve blood clots, most notably in heart attack victims. It is a fibrin-dependent serine protease which catalyzes the conversion of plasminogen to plasmin in one of the essential steps in the fibrinolytic cascade. The tPA enzyme was initially prepared from a variety of mammalian cell types, and was initially purified from human uterus (Rijken, D.C. et al. *Biochem Biophys Acta* (1979) 580:140–153) and from the Bowes melanoma cell line (Rijken, D.C. et al. *J Biol Chem* (1981) 256:7035–7041).

tPA is also known to be secreted naturally from a number of tissue sources including pig heart, fetal kidney, lung, and colon fibroblast cells. Recently, tPA has been produced using recombinant means by a number of groups, initiated by the successful cloning of the cDNA by Pennica, D. et al. *Nature* (1983) 301:214–221. The protein can be produced in a variety of hosts including *E. coli*, mouse L cells, CHO cells and yeast. (See, for example, EP Publication No. 174,835 (UpJohn), EP Publication No. 161,935 (Eli Lilly), EP Publication No. 143,081 (Ciba-Geigy), PCT application No. W086/05514 (Chiron).) Native tPA has been produced as disclosed by Snow Brand Milk Products (EP 196,226); Kochi Medical School (EP 194,736); Kowa KK and Asahi (EP 151,996); Meiji Milk Products (GB 2,153,366); Choay, S.A. (EP 133,070) and Asahi and Kowa KK (U.S. 4,505,893); and by Wakamoto Pharmaceutical (*Biotechnology*, Nov. 1986). Also relevant are two Genentech applications describing the production of tPA in CHO cells (EP 117,059 and EP 117,060).

Regardless of the manner in which tPA is produced, it is necessary to solubilize the protein to a workable concentration in aqueous solutions in order to administer small enough volumes to allow prompt administration of an effective dose. An effective dose is expected to be in the range of $1 \times 10^6 - 5 \times 10^7$ IU; highly purified tPA is expected to have a specific activity on the order of $2-5 \times 10^5$ IU per mg. Thus, in order to administer as little as 1 ml of a pharmaceutical composition, the solubility must be increased to at least about 5 mg per ml, and preferably to 50 mg per ml.

In addition, efficient purification of tPA produced by any of the foregoing cells requires a series of chromatographic procedures which are more efficiently conducted if a high level of solubility is maintained. For adaptation of purification procedures to tPA-containing medium, it would be desirable to achieve solubilities in these same ranges.

A variety of formulations for tPA has already been proposed. Many such formulations are concerned with stabilizing the tPA rather than enhancing its solubility. The proposed formulation most closely related to that disclosed hereinbelow is that set forth in EPO application Publication No. 217,379, published 8 Apr. 1987 to Mochida Pharmaceutical Co. Ltd. The formulations proposed are in arginine solution or a solution containing arginine and an acid addition salt. It appears that solubilities of the order of 10 mg/ml are achieved at arginine hydrochloride concentrations of approximately 0.5 M and above. As the arginine hydrochloride concentration is lowered, the solubility is diminished so that at 0.025 M arginine hydrochloride, only about 2 mg/ml dissolves. In the absence of arginine, in saline solution, less than 0.1 mg/ml solubility is exhibited. The pH of the formulation is not specified, but it is assumed to be that generated by arginine hydrochloride at the specified concentration.

The Mochida application also suggests that solubilities of the order of 10 mg per ml can be achieved at pH 7 in the presence of 0.1 M arginine hydrochloride and that somewhat higher concentrations can be achieved by supplementing the solution with high concentrations of salt. At lower pH (pH 2, pH 4) and higher pH (pH 9, pH 11), at lower arginine concentrations (0.25 M) comparable or diminished solubilities were found. The pH 4 solution was obtained by adjusting the arginine solution with citric acid.

Based on the Mochida disclosure, it would appear that the upper solubility limit in 0.1 M arginine is approximately 5 mg/ml.

DISCLOSURE OF THE INVENTION

The invention provides a formulation for tPA which permits solubility to be enhanced to level of approximately 50 mg/ml in relatively low concentrations of arginine. It has been found, quite surprisingly, that the addition of sodium citrate in an amount comparable to the low arginine concentration greatly improves the solubility characteristics of tPA. This increased solubility has permitted formulations for medical use to be of sufficient concentration that the drug can be administered by simple injection rather than by continuous intravenous feeding, and has permitted the efficient purification of tPA when produced in cell culture media, whether by cells which natively secrete it, or by using recombinant means.

Therefore, in one aspect, the invention is directed to a method to enhance the solubility of tPA in aqueous medium which method comprises providing, as excipients, arginine in a concentration of 0.02 to 0.2 M in combination with sodium citrate at a concentration of 0.02–0.08 at pH about 5–8, preferably pH 6. In another aspect, the invention is directed to compositions of tPA so formulated. In still another aspect, the invention is directed to an improved method to purify tPA wherein the improvement comprises manipulating a tPA solution containing the foregoing amounts of arginine and citrate.

MODES OF CARRYING OUT THE INVENTION

There are two major contexts in which the improvement in tPA solubility effected by the method of the invention is advantageous: formulations for administration of tPA by single injection and as an aid in solubilizing this material during purification.

With respect to formulation for administration, it is desirable that the amount of drug administered be included in a volume of 1 ml or less. Since a projected conventional dose is of the order of 5–50 mg, solubilities of these amounts in a single ml need to be achieved in order to make direct injection possible. If only, for example, 0.5 mg can be dissolved in a single ml, at least 10 ml of fluid must be administered. This is difficult to do in a single administration, and results in the patient being tied to an apparatus for intravenous injection, with all its discomforts.

EPO application 217,379 discloses the solubility enhancing effects of arginine on tPA. According to that disclosure, a solubility of 10 mg/ml can be achieved in the presence of very high concentrations of arginine hydrochloride—i.e., 0.5–1 M. These levels of arginine are entirely unsuitable for administration to human subjects for several reasons. First, because arginine in practical amounts is obtained from microbial sources, it is a potential carrier of endotoxins. Second, even as prepared from fermentation broth, arginine is quite expensive and increases the cost of the dosage regimen. Finally, the presence of such arginine concentrations in the administered composition may diminish the effective activity of the tPA by reducing its affinity for appropriate carbohydrate receptors in a manner analogous to its capacity to elute tPA from Sepharose columns. Elevated levels of arginine in systemic administration could reduce tPA's affinity for fibrim binding. In addition, solutions of 1 M arginine are quite viscous and impede gel filtration.

It has been found, as described hereinbelow, that by addition of a suitable amount of citrate salt to the arginine hydrochloride formulation, the concentration of arginine hydrochloride required can be reduced by more than a factor of 10 to provide a composition which is of practical value in pharmaceutical practice. The formulation contains total salt concentration provided by the arginine hydrochloride and sodium citrate, for example, of the order of physiological ionic strength, thus avoiding any incompatibility due to this differential with the injected material.

The explanation for the ability of the citrate salt to enhance tPA solubility in the presence of arginine is not clear, and applicants commit themselves to no theory. However, it is known that citrate is an antioxidant (although alternative anti-oxidants, such as ascorbic acids are not effective) and that it is capable of chelating cations which might otherwise catalyze oxidation of free-SH groups (although EDTA, a known chelator, is also ineffective). The function of the citrate may be to stabilize the tPA protein structure through hydrogen bonding or may be due to some other effect.

In any event, the tPA protein, however prepared and purified, is dissolved for administration in an amount between 5–50 mg/ml in the presence of arginine hydrochloride or other arginine inorganic salt at a concentration of 0.02–0.2 M of arginine or argininium ion and an inorganic salt of citrate, preferably sodium citrate at a concentration of 0.02–0.08 M. Other soluble citrate salts, such as potassium citrate, could, of course, also be used. A particularly preferred formulation contains 0.15 M arginine hydrochloride and 0.05 M sodium citrate.

The concentrations used to describe the compositions are given in terms of the organic moieties—it is understood that the distribution of ionic states depends on the pH of the solution. Other basic amino acids such as lysine and ornithine can be substituted for arginine in these compositions, but the results are not as good, and these compositions are much less preferred. It is clear that alternative organic acid salts, such as acetates, cannot substitute for citrate. The pH of the composition is 5–8, preferably pH 6.

The formulations of the invention may also be supplemented with other additives such as buffers, stabilizers, wetting agents, and so forth, so long as these additives are nontoxic and do not interfere with the solubilizing effect of the arginine/citrate excipients.

The other circumstance in which a high solubility for tPA is desirable is in the context of preparation and purification of the product from cell culture medium.

A wide variety of purification processes may be used, but most of these involve, at least in part, chromatographic procedures, gel filtrations, ammonium sulfate precipitations and the like. All of these procedures are greatly aided by decreasing the total volume required. The inconvenience of running chromatographic columns, for example, of course increases as the volume of material which needs to be passed over them is increased. The use of arginine hydrochloride alone in this context is workable but quite difficult because of its viscosity. In order for 1 M arginine to be used, for example, high pressure needs to be applied to obtain reasonable flow rates.

Initially, it may not be necessary to deliberately solubilize the tPA in the culture medium, since the production levels are often quite low in net concentration—i.e., of the order of less than 1 mg/ml. Nevertheless, as soon as some purification is achieved, the concentration of tPA increases and solubilization may be needed if smaller volumes are to be employed.

Typical purification procedures for tPA from "native" sources are found, for example, in Binder, B.R., et al, *J Biol Chem* (1979) 254:1998–2003; Rijken, D.C., et al, *J Biol Chem* (1981) 256:7035–7041 and Strickland, D.K., et al, *Biochemistry* (1983) 22:4444–4449.

Recombinant tPA has been purified using similar procedures, i.e., involving analogous, though perhaps differently combined, process steps. In all cases, once a high level of purity is achieved, it is advantageous to solubilize the tPA to relatively high concentrations so that reasonable volumes can be used, especially in chromatographic steps. Of particular interest is the elution of Type I and Type II tPA from lysine-sepharose columns using an arginine gradient, as reported by Rijken, D.C., et al, *Thrombosis and Hemostatis* (1985) 54:788–791. In this elution, greater solubilization of the eluate can be obtained by the addition of citrate, according to the method of the invention.

Thus, as applied either to pharmaceutical formulations or to tPA purification, supplementation with a citrate salt is highly desirable.

EXAMPLES

The following examples are intended to illustrate but not to limit the invention.

EXAMPLE 1

Solubility of Recombinant tPA in Arginine HCl Alone

Recombinant tPA produced in CHO cells was purified to apparent homogeneity and stored at approximately 1 mg/ml as measured by an ELISA assay with anti-tPA antibodies. The pH of the solution, which contained 1.0 arginine hydrochloride was adjusted to either pH 6 or pH 5 and the samples were concentrated to maximum solubility using an Amicon-Centicon concentrator. After maximum concentration, the solution at pH 6 showed tPA content (by ELISA) of approximately 33 mg/ml; that at pH 5 showed a solubility for tPA measured by ELISA at 41.5 mg/ml. A second determination using the same protocol showed that material could be concentrated to a level of approximately 57 mg/ml as measured by ELISA, while the pH 5 sample was concentrated to about 43 mg/ml.

EXAMPLE 2

Effect of Arginine Concentration on Solubility

Similar determinations were made using purified CHO produced tPA which was dialyzed against 0.1 M arginine hydrochloride, pH 5 and pH 6 and against 0.5 M arginine, pH 5 or pH 6. Dialysates containing 0.5 M arginine supported about 15 mg/ml tPA (pH 5) and 39 mg/ml tPA (pH 6); in 0.1 M arginine, only about 1-1.5 mg/ml was soluble.

EXAMPLE 3

Effect of Sodium Citrate

Samples of purified CHO tPA at an initial protein concentration of about 0.5 mg/ml were concentrated from media containing, respectively, 0.15 M arginine, pH 6 alone and this concentration of arginine along with 0.05 M sodium acetate or sodium citrate.

Each of the foregoing solutions was concentrated to the maximum solubility for tPA. The presence of 0.15 M arginine alone did not permit concentration to an appreciably higher solubility than the original 0.5 mg/ml; the addition of 50 mM sodium acetate permitted an increase in concentration to about 1.3 mg/ml. However, when sodium citrate at 50 mM was added, the solution could be concentrated to a solubility of 18 mg/ml tPA.

We claim:

1. A method to enhance the solubility of tissue plasminogen activator (tPA) in aqueous medium, which method comprises dissolving said tPA in an aqueous medium containing a basic amino acid at a concentration of 0.02-0.2 M and a citric acid moiety at a concentration of 0.02-0.08 M, at a pH of 5-8.

2. The method of claim 1 wherein the basic amino acid is arginine.

3. The method of claim 1 wherein the basic amino acid concentration is approximately 0.15 M.

4. The method of claim 1 wherein the citric acid moiety is provided as sodium citrate and the concentration of the citric acid moiety is approximately 50 mM.

5. An improved method to purify tPA by chromatographic or gel filtration steps wherein the improvement comprises conducting the purification on a solution of tPA, wherein said solution further contains 0.02-0.2 M of a basic amino acid and 0.02-0.08 M of a citric acid moiety.

6. A composition of matter which comprises 10-50 mg/ml dissolved tPA in an aqueous medium, which medium contains 0.02-0.2 M of arginine and 0.02-0.08 M of a citric acid moiety at pH 5-8.

7. The composition of claim 6 wherein the arginine concentration is approximately 0.15 M.

8. The composition of claim 6 wherein the citric acid moiety is provided as sodium citrate and the concentration of the citric acid moiety is approximately 0.05 M.

* * * * *